Oct. 21, 1969 S. ROBISON ETAL Plant Pat. 2,934
APPLE TREE
Filed Dec. 11, 1968
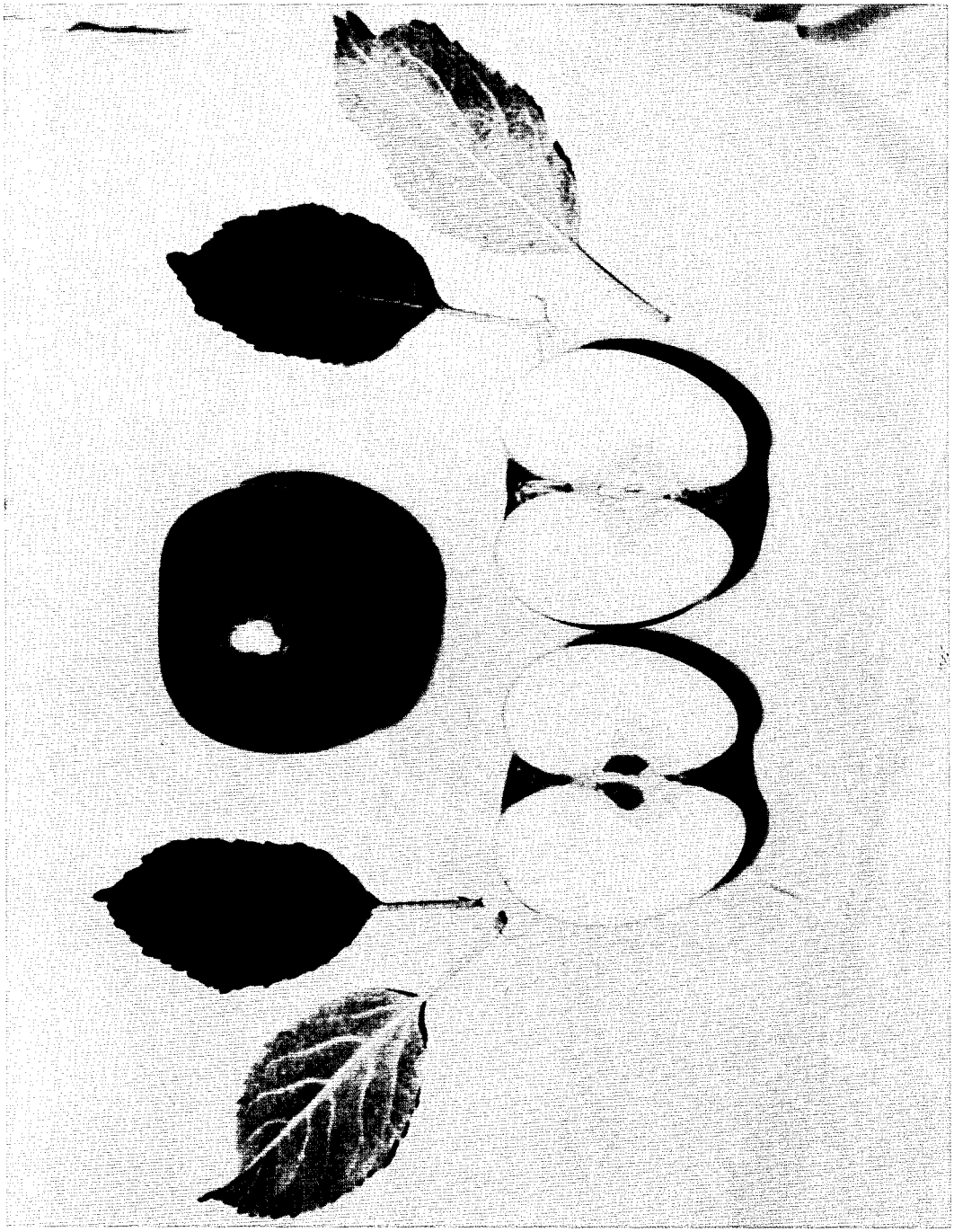
Inventors.
Stanley Robison
Ivan E. Wallace
By: Robb & Robb
Attorneys.

United States Patent Office

Plant Pat. 2,934
Patented Oct. 21, 1969

2,934
APPLE TREE

Stanley Robison and Ivan E. Wallace, Caldwell, Idaho, assignors to Hill Top Orchards and Nurseries, Inc., Hartford, Mich., a corporation of Michigan

Continuation-in-part of application Ser. No. 617,425, Feb. 20, 1967. This application Dec. 11, 1968, Ser. No. 800,787

Int. Cl. A01h *5/08*

U.S. Cl. Plt.—34 1 Claim

This invention is a continuation-in-part of our earlier filed application Ser. No. 617,425, filed Feb. 20, 1967, which is to be abandoned effective with the filing of the continuation-in-part application.

The invention relates to a new and distinct variety of apple tree which was discovered by us as a limb sport of the variety of apple tree known as "Blackjon" (unpatented), said discovery having been made in an orchard which was being cultivated and maintained as a part of an operating ranch near Caldwell, Idaho, owned by one of us and supervised by the other of us.

Our attention was attracted to the new sport by its earlier coloring fruit borne on the sport limb. Steps were promptly taken by use to preserve the sport, as well as to topwork and bud the same to other trees, as performed by us and on our behalf at Caldwell and Fruitland, Idaho, and elsewhere. Continued observations of the original sport and the progeny thereof derived by top-working and budding for several generations, convinced us that its earlier fruit coloring and earlier picking season, ranging from about 10 days to 2 weeks earlier than the fruit of "Blackjon," were fixed and established and were transmissible through succeeding propagations.

While our new sport generally resembles the parent variety "Blackjon" in some respects other than the earlier coloring and earlier picking characteristics aforementioned, it is definitely distinguishable therefrom and from another somewhat similar variety known as "Nured" (Plant Patent No. 2,650) which is another earlier coloring sport of "Blackjon," as well as distinguished from all other apple varieties of which we are aware, as evidenced by the following unique combination of characteristics which are particularly outstanding in our new sport:

(1) Larger, less deeply incised and darker green leaves than those of "Blackjon" and "Nured";

(2) An earlier fruit coloring and picking season ranging from about 10 days to 2 weeks earlier than the fruit of "Blackjon," with the fruit usually beginning to color about one month from bloom and being darker red in color until near the picking season than the fruit of "Blackjon" and "Nured"; and (3) A lighter, brighter and more attractive red fruit color at the mature fruit stage than the fruit of "Blackjon" and "Nured," with the color being distributed as a smooth red wash with few minute faint stripes, as compared to the strongly striped color pattern of mature fruit of "Blackjon" and "Nured."

The accompanying drawing shows typical specimens of the fruit and foliage of our new variety, with the fruit being illustrated in both elevation and in longitudinal cross-section, and with the leaf specimens illustrating both the upper and under surfaces thereof, all as depicted in color as nearly true as it is reasonably possible to make the same in a color illustration of this character.

The following is a detailed description of our new apple variety, with color terminology in accordance with the Nickerson Color Fan, published by Munsell Color Company, Inc., of Baltimore, Maryland, except where general color terms of ordinary dictionary significance are obvious.

Parentage: Sport of "Blackjon."

Locality where observations were made: Fruitland, Idaho and Hartford, Mich.

Dates of first and last pickings: About August 25 and September 5, respectively, when the parent variety in the same orchard was first and last picked about September 10 and September 20, respectively.

Tree: Medium size; vigorous; spreading; medium dense; vase formed; rapid grower; hardy; productive; regular bearer.

*Trunk.*—Medium stockiness; medium smoothness.

*Branches.*—Medium thickness; medium smoothness; much-branched. Color—gray. Lenticels—numerous; medium size.

*Leaves.*—Medium size; oval; abruptly pointed; medium thickness; rugose. Length—from 3 inches to 3½ inches. Width—from 1¼ inches to 1½ inches. Color—dark green. margin—slightly crenate; dully serrate. Petiole—medium length; medium thickness.

Flowers:

*Dates of first and full bloom.*—About April 25 and May 10, respectively. *Size.*—medium. *Color.*—pink.

Fruit:

*Maturity when described.*—Eating hard ripe; about August 25.

*Size.*—Uniform. Axial diameter—from 2¼ inches to 2¾ inches. Transverse diameter—from 2½ inches to 3 inches.

*Form.*—Uniform; symmetrical; regular; oblate; truncate at base and apex; ovid; slightly ribbed.

*Cavity.*—Symmetrical; acute. Depth—from ½ inch to ¾ inch. Breadth—from ⅜ inch to ½ inch. Markings—small amount of light russeting.

*Basin.*—Symmetrical; abrupt; narrow; 5-crowned.

*Stem.*—Clubbed; medium stoutness. Length—about ¾ inch or less. Bracts—present; 2 in number.

*Calyx.*—Closed; segments persistent; from acute to acuminate; approximate at base; erect; connivent. Outer surface—pubescent. Inner surface—pubescent.

*Skin.*—Medium thickness; tough; smooth; glossy. Dots—conspicuous; few; large; ruptured; circular; color—whitish cream; distribution—more numerous on apical than basal end. Ground color — yellow. Color markings — faintly striped; bright; color—basically from near bright Moderate Red, Hue 2.5R 4/10 to near bright Strong Red, Hue 5R 4/12, with some purplish overcast, at maturity, but usually darker during earlier stage of immaturity. Bloom—warning. Scrafskin—wanting. General color effect—over-all bright red, with very slight striping apparent.

*Flesh.*—Juicy. Color—white, with yellowish tint. Texture—firm; fine; crisp. Flavor—acid; rich. Aroma—distant. Quality—best.

*Core.* — Median. Bundle area (longitudinal section)—medium large; ovate; cordate; symmetrical at base; alternate with cell. Halves of area—equal. bundles—inconspicuous; color—green. Alternate bundle — above stamens. Core lines — meeting; cross section—distinct. Carpillary area—distinct; medium size.

*Calyx tube.*—Pubescent; narrowly cone-shaped.

*Stem of funnel.*—Short.

*Depth of tube to shoulder.*—½ inch.

*Entire depth.*—½ inch.

*Styles.*—Distinct; pubescent.

*Stamens.*—In one distinct whorl; median.

*Auxiliary cavity.*—Wanting.

*Seed cells.*—Abaxile; open. Cell walls—thin; tough; length—3/8 inch; breadth—3/16 inch. Longitudinal section—broadly ovate. Surface—smooth. Cross section—broad.

*Seeds*—6–8 perfect; not over 2 per cell. Length—1/4 inch. Breadth—1/8 inch. Form—acute. Color—reddish brown.

Use: Dessert; culinary.

Keeping quality: Good; up to 3½ months in ordinary storage.

Resistance to insects and disease: Medium resistance to usual insects and diseases to which apple varieties are normally subject, but some susceptibility to fire blight and powdery mildew, as determined by comparison with other varieties grown under the same conditions in Idaho and Michigan.

General observations and comparisons: The following distinctions between our new sport and its parent "Blackjon" and "Nured" are clearly notable:

*Vegetative characteristics (leaf and shoot).*—New bark—more brownish in color than in "Blackjon" and "Nured." Lanticels—fewer in number than in "Blackjon" and "Nured"; color—white, while those of "Nured" are brown. Leaf blades—substantially longer and broader over-all than those of "Blackjon" and "Nured," and thicker than those of "Nured." Leaf base—wider and more even than in "Blackjon" and "Nured." Leaf apex—more full and more abruptly acute, contrary to narrow and gradually acute leaf apex in "Blackjon" and "Nured." Upper surface of leaf blades—less pubescent than in "Blackjon" and "Nured." Leaf serrations—more dully serrate to crenate and more regular than the more deeply and irregularly incised leaves of "Blackjon" and "Nured." Leaf color—deeper green than leaf color of "Blackjon" and "Nured." Bud scales (on 2-year old spurs)—brown in color and moderately pubescent, while those of both "Blackjon" and "Nured" are green and very pubescent. Terminal buds—twice as large as those of "Nured."

*Fruit (about 1 month before maturity).*—Stem cavity—narrower and shallower than in fruit of "Nured." Shoulder—less distinctly corrugated than in "Nured." Lenticels—fewer but more conspicuous than in both "Blackjon" and "Nured." Apical end—more distinctly crowned or 5-pointed than in both "Blackjon" and "Nured." Calyx lobes—smaller (about ½ size) than in "Blackjon" and "Nured," lighter green and less pubescent than those of "Nured," and more erect and connivent than those of "Blackjon." Basin—small, regular and shallow, while those of "Blackjon" are wider and of medium depth, and those of "Nured" are angular, wide, abrupt and deep. Color—begins to color by the time fruit is one month from bloom and fruit is darker red at later immature stage than "Blackjon" fruit which does not begin to color until about 6 weeks before harvest and does not attain its dark red color until 1 or 2 days before harvest, and fruit of our new variety is darker red in color than "Nured" fruit at the same immature stage.

*Fruit (mature).*—Cheek—waxen, with a fine finish, and little or no scarfskin, while that of "Nured" fruit has patches and flecks of scarfskin, with cuticle much cracked. Dots—less numerous but more conspicuous than in "Blackjon," while "Nured" dots are more numerous, smaller in size and not haloed as in our new sport. Basin—more chowned, deep, with 5 pronounced grooves and cuticle broken into striated concentric rings, but not rough, while basin in "Blackjon" and "Nured" is wide, abrupt, deep, irregularly grooved, with cuticle broken into striated concentric rings but not rough in "Blackjon," but much cracked and slightly rough in "Nured." Lobes—greenish in color, moderately pubescent, flat with reflexed tips, while those of "Blackjon" and "Nured" are more grayish green, heavily pubescent, and tips are much twisted and rolled. Calyx tube—V-shaped, while that of "Blackjon" and "Nured" is funnel shaped. Core lines—meeting and cordate, while those of "Blackjon" and "Nured" are meeting but oblate. Skin color—brighter and lighter red color than skin of "Blackjon" and "Nured" at mature stage, with color pattern more smooth, but with some minute faint stripes, whereas "Blackjon" and "Nured" color pattern is very strongly striped and presents a strong contrast between lighter and darker red stripes; our new variety has more yellow ground color in the fruit skin, which makes the red color appear brighter and lighter than in "Nured" at the mature stage.

We claim:

1. A new distinct variety of apple tree, substantially as herein shown and described, characterized particularly as to novelty by its general resemblance in some respects to its parent variety "Blackjon," but being significantly distinguished therefrom and from the variety known as "Nured" (Plant Patent No. 2,650) by the unique combination of larger, less deeply incised and darker green leaves than those of "Blackjon" and "Nured," an earlier fruit coloring and picking season ranging from about 10 days to 2 weeks earlier than the fruit of "Blackjon" with the fruit usually beginning to color about one month from bloom and being darker red in color until near the picking season than the fruit of "Blackjon" and "Nured," and a lighter, brighter and more attractive red fruit color at the mature fruit stage than the fruit of "Blackjon" and "Nured," with the color being distributed as a smooth red wash, with minute faint stripes, as compared to the strongly striped color pattern of mature fruit of "Blackjon" and "Nured."

No references cited.

ROBERT E. BAGWILL, Primary Examiner